(12) United States Patent
Austin et al.

(10) Patent No.: US 10,910,089 B2
(45) Date of Patent: Feb. 2, 2021

(54) METHODS AND SYSTEMS PROVIDING CENTRALIZED ENCRYPTION KEY MANAGEMENT FOR SHARING DATA ACROSS DIVERSE ENTITIES

(71) Applicant: Universal Patient Key, Inc., Sterling, MA (US)

(72) Inventors: Joseph R. Austin, Sterling, MA (US); Shahir Kassam-Adams, Lovingston, VA (US)

(73) Assignee: UNIVERSAL PATIENT KEY, INC., Sterling, MA (US)

( * ) Notice: Subject to any disclaimer, the term of this patent is extended or adjusted under 35 U.S.C. 154(b) by 1048 days.

(21) Appl. No.: 15/045,605

(22) Filed: Feb. 17, 2016

(65) Prior Publication Data

US 2016/0275309 A1   Sep. 22, 2016

Related U.S. Application Data (60) Provisional application No. 62/136,196, filed on Mar. 20, 2015.

(51) Int. Cl.
*G06F 21/62* (2013.01)
*G16H 10/60* (2018.01)
(Continued)

(52) U.S. Cl.
CPC ......... *G16H 10/60* (2018.01); *G06F 21/6254* (2013.01); *G06Q 20/382* (2013.01);
(Continued)

(58) Field of Classification Search
CPC .. G06Q 20/00–425; G06Q 2220/00–10; H04L 9/00–38; H04L 2209/00–88; G16H 10/00–60; G06F 21/00–88
See application file for complete search history.

(56) References Cited

U.S. PATENT DOCUMENTS 5,892,900 A * 4/1999 Ginter .................. G06F 21/10
                                              726/26
6,397,224 B1   5/2002 Zubeldia et al.
(Continued)

OTHER PUBLICATIONS http://mist-deid.sourceforge.net/ "MIST—The MITRE Identification Scrubber Toolkit".
(Continued)

*Primary Examiner* — Calvin L Hewitt, II
*Assistant Examiner* — Chenyuh Kuo
(74) *Attorney, Agent, or Firm* — Morse, Barnes-Brown & Pendleton, P.C.; Sean D. Detweiler, Esq.

(57) ABSTRACT

A method and apparatus provide centralized encryption key management for sharing data across diverse entities. In particular, the present invention relates to a universal and regulatory compliant system and method for sharing personal data records across diverse entities while maintaining unique identifiers at each entity for protecting the identity of any particular person. The present invention enables multiple organizations to be able to share their respective disparate data in a manner in which the disparate personal data records can be aggregated and manipulated by a single entity without putting the personal data records at risk.

7 Claims, 6 Drawing Sheets

(51) Int. Cl.
  *G06Q 20/38* (2012.01)
  *H04L 29/06* (2006.01)
  *H04L 9/32* (2006.01)
  *H04L 9/14* (2006.01)

(52) U.S. Cl.
  CPC ............ *H04L 9/3239* (2013.01); *H04L 63/06* (2013.01); *G06Q 2220/00* (2013.01); *H04L 9/14* (2013.01); *H04L 2209/42* (2013.01); *H04L 2209/76* (2013.01); *H04L 2209/88* (2013.01)

(56) References Cited

U.S. PATENT DOCUMENTS

| | | | |
|---|---|---|---|
| 6,732,113 | B1 | 5/2004 | Ober et al. |
| 6,734,886 | B1 | 5/2004 | Hagan et al. |
| 6,804,787 | B2 | 10/2004 | Dick |
| 7,120,928 | B2 | 10/2006 | Sheth et al. |
| 7,269,578 | B2 | 9/2007 | Sweeny |
| 7,376,677 | B2 | 5/2008 | Ober et al. |
| 7,428,706 | B2 | 9/2008 | Hagan et al. |
| 7,519,591 | B2 | 4/2009 | Landi et al. |
| 7,526,485 | B2 | 4/2009 | Hagan et al. |
| 7,543,149 | B2 | 6/2009 | Ricciardi et al. |
| 7,587,366 | B2 | 9/2009 | Grim, III et al. |
| 7,668,835 | B2 | 2/2010 | Judd et al. |
| 7,711,120 | B2 | 5/2010 | Kimmel et al. |
| 7,792,517 | B2 | 9/2010 | Mowry et al. |
| 7,827,234 | B2 | 11/2010 | Eisenburger et al. |
| 7,865,376 | B2 | 1/2011 | Ober |
| 7,945,048 | B2 | 5/2011 | Ricciardi et al. |
| 8,024,339 | B2 | 9/2011 | Barker et al. |
| 8,037,052 | B2 | 10/2011 | Kariathungal et al. |
| 8,042,193 | B1 | 10/2011 | Pilouras |
| 8,069,053 | B2 | 11/2011 | Gervais et al. |
| 8,090,595 | B2 | 1/2012 | Hartman |
| 8,121,984 | B2 | 2/2012 | Barbieri |
| 8,176,334 | B2 | 5/2012 | Vainstein |
| 8,275,850 | B2 | 9/2012 | Kohan et al. |
| 8,296,299 | B2 | 10/2012 | Haskell et al. |
| 8,296,341 | B2 | 10/2012 | Hagan et al. |
| 8,341,427 | B2 | 12/2012 | Auradkar et al. |
| 8,355,923 | B2 | 1/2013 | Gervais et al. |
| 8,364,969 | B2 | 1/2013 | King |
| 8,381,287 | B2 | 2/2013 | Trotter |
| 8,473,452 | B1 | 6/2013 | Ober et al. |
| 8,494,874 | B2 | 7/2013 | Green, III et al. |
| 8,560,456 | B2 | 10/2013 | Williams |
| 8,566,113 | B2 | 10/2013 | Friedlander et al. |
| 8,577,933 | B2 | 11/2013 | Evenhaim |
| 8,589,437 | B1 | 11/2013 | Khomenko et al. |
| 8,661,249 | B2 * | 2/2014 | Guarraci ................. H04L 9/083 713/168 |
| 9,292,707 | B1 | 3/2016 | Fontecchio |
| 9,614,814 | B2 † | 4/2017 | Fontecchio |
| 9,830,476 | B2 | 11/2017 | Fontecchio |
| 2002/0073138 | A1 | 6/2002 | Gilbert et al. |
| 2002/0173971 | A1 | 11/2002 | Stirpe et al. |
| 2006/0053032 | A1 | 3/2006 | Weiler et al. |
| 2007/0162377 | A1 | 7/2007 | Williams |
| 2008/0147554 | A1 | 6/2008 | Stevens et al. |
| 2009/0106550 | A1 | 4/2009 | Mohamed |
| 2009/0287502 | A1 | 11/2009 | Roberts et al. |
| 2010/0070306 | A1 | 3/2010 | Dvorak et al. |
| 2010/0094758 | A1 | 4/2010 | Chamberlain et al. |
| 2010/0114607 | A1 | 5/2010 | Kress |
| 2010/0205009 | A1 | 8/2010 | Kostoff |
| 2010/0211781 | A1 | 8/2010 | Auradkar et al. |
| 2010/0223467 | A1 | 9/2010 | Dismore et al. |
| 2010/0256994 | A1 | 10/2010 | Eisenberger et al. |
| 2011/0191245 | A1 | 8/2011 | Ricciardi et al. |
| 2012/0036360 | A1 | 2/2012 | Bassu et al. |
| 2012/0116800 | A1 | 5/2012 | McCallie et al. |
| 2012/0124637 | A1 | 5/2012 | Dunaway |
| 2012/0226916 | A1 | 9/2012 | Hahn et al. |
| 2012/0316898 | A1 | 12/2012 | Levitt et al. |
| 2013/0117126 | A1 | 5/2013 | Coppinger |
| 2013/0117128 | A1 | 5/2013 | Coppinger |
| 2013/0246097 | A1 | 9/2013 | Kenney et al. |
| 2013/0304504 | A1 | 11/2013 | Powel |
| 2013/0304542 | A1 | 11/2013 | Powel |
| 2013/0346104 | A1 | 12/2013 | Pillai |
| 2014/0013452 | A1 | 1/2014 | Aissi et al. |
| 2014/0040308 | A1 | 2/2014 | Ober et al. |
| 2014/0041047 | A1 | 2/2014 | Jaye et al. |
| 2014/0108049 | A1 | 4/2014 | Fuhrmann et al. |
| 2014/0108258 | A1 | 4/2014 | Williams |
| 2014/0122873 | A1 | 5/2014 | Deutsch et al. |
| 2015/0095243 | A1 | 4/2015 | Eiler et al. |
| 2015/0149208 | A1 † | 5/2015 | Lynch |
| 2016/0110648 | A1 | 4/2016 | Baveja et al. |
| 2016/0147945 | A1 † | 5/2016 | MacCarthy |
| 2016/0267238 | A1 * | 9/2016 | Nag ........................ G16H 10/60 |
| 2016/0344544 | A1 | 11/2016 | Biesinger et al. |
| 2017/0103179 | A1 | 4/2017 | Jiao et al. |

OTHER PUBLICATIONS

Non-Final Office Action from U.S. Appl. No. 16/135,972, dated Aug. 13, 2020.

* cited by examiner
† cited by third party

METHODS AND SYSTEMS PROVIDING CENTRALIZED ENCRYPTION KEY MANAGEMENT FOR SHARING DATA ACROSS DIVERSE ENTITIES

CROSS-REFERENCE TO RELATED APPLICATION(S)

This application claims priority to, and the benefit of, U.S. Provisional Application 62/136,196, filed Mar. 20, 2015, for all subject matter common to both applications. The disclosure of said provisional application is hereby incorporated by reference in its entirety.

FIELD OF THE INVENTION

The present invention relates to methods and systems providing centralized encryption key management for sharing health related data across diverse entities. In particular, the present invention relates to a universal and regulatory compliant method for sharing personal data records across diverse entities while maintaining unique identifiers at each entity for protecting the identity of any particular person.

BACKGROUND

Generally, regulations and laws protecting the privacy of personal data have created a plethora of strategies for protecting the identity of personal data. Typically, institutions, organizations, and businesses that create personal data have their own methods for complying with identity protection laws. These methods may include in-house developed proprietary methods, or one of many disparate off the shelf solutions. The current methods utilized for protecting personal data have been responsible for serious identity breaches resulting in the theft of customer and employee personal information. Conventional methods implement processes of de-identification by the use of hashing methods applied to strings of characters generated from private data elements in data records. These conventional processes are built using a single hashing seed or encryption key, which is shared across many disparate target sites. Such systems suffer the risk that the resulting generated values can be mapped back to the original source data. Once a breach has occurred, all the target data sites have exposed values which, in themselves, could become regulated data values.

Additionally, the personal data records stored by the various entities cannot be shared or aggregated for any meaningful or useful data analysis. Specifically, the personal data cannot be shared between entities where the identity any one particular individual is of no importance. A problem associated with protected personal data is easily recognizable in the industries related to healthcare where each provider or insurer typically employs their own proprietary methods for de-identifying personal data records, making it nearly impossible to do any meaningful aggregations of the data for important clinical research or cost analysis at higher regional, state, or national levels. This problem is compounded by the fact that there are many separate and distinct companies involved with the care of an individual patient, making it difficult to share and or tie the information together for a single patient once the stake holder has applied their own proprietary de-identification process to the patient's personal data records.

These and other shortcomings described herein existing in the conventional approaches to sharing personal, private, or otherwise protected data area a problem that would not exist but for the present need for and utilization of computer technology handling such data. With so many distinct, distributed, and/or disparate forms of data and computer systems managing the data, the difficulties in handling such data in a way that provides desired access and utilization of the data without violating privacy guidelines or putting personal data records at risk have been caused by the implementation of the computer technology that prior to the present invention conventionally handled such data.

SUMMARY

There is at least a need for a capability to map disparate data sets from multiple sources at a single entity to provide the entity with access to the total collection of the disparate data sets. In particular, there is a need for multiple organizations, including those having separate networks and systems, to be able to share their respective disparate data in a manner in which the disparate personal data records can be aggregated and manipulated by a single entity without putting the personal data records at risk. Specifically, there is a need for organizations to fully comply with regulatory mandates for the protection of personal identity in a manner that still allows for the optional sharing of personal data for the purposes of important research, aggregation, and analysis, without violating such mandates. The present invention is directed toward further solutions to address these needs, in addition to having other desirable characteristics.

The present invention enables organizations to share their disparate personal data records by implementing a consistent multi-tier de-identification and encryption architecture. Specifically, a centralized key management service provides a trusted secure site to manage key ownership and sharing between disparate entities. A decentralized process uses authorized encryption keys to standardize shareable tokens at partnering entity sites. Personal data records created and stored at de-centralized locations, at the entity site, use the encryption or site key information provided by the centralized key management architecture to enable secure sharing of their respective personal data records. The central key management architecture does not maintain de-centralized token data and only serves as a management hub for the distribution of encryption keys and standardization of tokens at an entity site level.

Overall, the invention provides a standard and consistent method of securely encoding and encrypting a person's identity, in personal data records, in a manner that is unique to each data source combined with a method for each entity data source to produce a compatible set of personal data records to any other data source. Accordingly, the invention dramatically improves upon existing processes by enabling entity site level encryption to linking tokens while still allowing for sharing of personal data records between multiple entities. The improved processes provide technological improvements to fields related to personal data privacy, encryption, and secure analysis of aggregated data from disparate entities. Additionally, the present invention allows disparate parties to share personal data between one another in a secure manner and in compliance with strict privacy requirements using one or more computer hardware devices. The technological improvements provide a technical solution to the technological problems related to personal data privacy and security, in particular, maintaining personal data privacy for personal data being shared over disparate computer hardware systems and between disparate parties. The technological solution is provided through a combination of unconventional steps and processes performed as discussed herein, using one or more computer hardware devices in accordance with the present invention.

In accordance with an embodiment of the present invention, a method for distributing personal health data is provided. The method includes receiving at a source client device, using a processor, a distributed software engine from a key management system. The distributed software engine includes an encryption token, a source client device encryption key unique to the source client device, at least one destination client device encryption key unique to a destination client device, and a processing template. The method further includes executing, using a processor, the processing template. Executing the processing template includes de-identifying personal health data. De-identifying personal health data includes standardizing the personal health data into standardized personal health data, combining the standardized personal health data with the encryption token to create a personal identifier hash value, and encrypting the personal identifier hash value using the source client device encryption key unique to the source client device. Executing the processing template also includes determining the at least one destination client device encryption key unique to the destination client device and transforming the encrypted personal identifier hash value from a source client encryption key format to at least one destination client device encryption key format unique to the destination client device. The method also includes transmitting, using a processor, the transformed personal identifier hash value to the destination client device.

In some implementations, the distributed software engine is compiled specifically for the source client device. In some implementations, the each step of the execution, the processing template is performed in process. In some implementations, transforming the encrypted personal identifier hash value is performed prior to transmission to the destination client device. In some implementations, the key management system is a trusted centralized third party server. In some implementations, the distributed software engine further includes requesting a password to access at least one of the encryption token, the source client device encryption key, the at least one destination client device encryption key, and the processing template included in the distributed software engine. In some implementations, the distributed software engine further includes requesting the encryption token, the source client device encryption key, the at least one destination client device encryption key, and the processing template from a centralized data vault. In some implementations, the registering further comprises including a client device encryption key and a client device identifier. In some implementations, the method further includes receiving a request from the destination client device to share the personal health data.

In accordance with an embodiment of the present invention, a system for managing universally shareable personal health data in compliance with legal and regulatory requirements is provided. The system includes a key management system comprising a storage device for storing a plurality of site level encryption keys and business rules. The key management system is operable to register two or more entities for sharing the personal health data, determine legal and regulatory requirements associated with the business rules for the two or more entities and determine two or more unique encryption keys of the plurality of site level encryption keys for each of the two or more entities based on the legal and regulatory requirements. The key management system is also operable to transmit the two or more unique encryption keys associated with each client device of the at least one of the two or more entities and compile a distributed software engine for each of the two or more entities for facilitating secure sharing of the personal health data between the two or more entities. The distributed software engine comprises an encryption token, a source client device encryption key, at least one destination client device encryption key, and a processing template to be used for the facilitating.

In some implementations, the key management system is operable to execute the processing template. In some implementations, the processing template includes instructions for de-identifying personal health data. De-identifying health data includes standardizing the personal health data into standardized personal health data, combining the standardized personal health data with the encryption token to create a personal identifier hash value, and encrypting the personal identifier hash value using the source client device encryption key unique to the source client device. Executing the processing template also includes determining the at least one destination client device encryption key unique to the destination client device. Executing the processing template further includes transforming the encrypted personal identifier hash value from a source client encryption key format to at least one destination client device encryption key format unique to the destination client device. In some implementations, executing each step of the executing the processing template is performed in process. In some implementations, executing the transforming the encrypted personal identifier hash value is performed prior to transmission to the destination client device.

In some implementations, the distributed software engine is compiled specifically for the source client device. In some implementations, the key management system is a trusted centralized third party server. In some implementations, the distributed software engine requests a password to access at least one of the encryption token, the source client device encryption key, the at least one destination client device encryption key, and a processing template included in the distributed software engine. In some implementations, the distributed software engine requests the encryption token, the source client device encryption key, the at least one destination client device encryption key, and a processing template from a centralized data vault. In some implementations, key management system registers a client device encryption key and a client device identifier. In some implementations, the key management system receives a request from the destination client device to share the personal health data.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to a centralized key management system that manages encryption keys for a plurality of de-centralized entity client computing devices to enable sharing between the plurality of de-centralized entities. In particular, the centralized key management system acts as a trusted third party management hub for the encryption keys, entity client computing device identifiers, and other information to be distributed for use by the de-centralized entities. Accordingly, the centralized key management system is operable to facilitate the sharing of secure encoded and encrypted personal data records (e.g., personal healthcare data records) between a plurality of disparate entities in a manner such that the key management system does not store or process the personal data records itself.

The disparate entities in the present invention may represent institutions, organizations, and/or businesses, each using a combination of different proprietary and commercially available data storage systems for storing personal data records while also complying with identity protection laws. For example, the institutions, organizations, and/or business may be providers in the health care field which maintain various personal healthcare records maintained in the healthcare field for patients and/or customers. The personal healthcare records are required to be stored according to various privacy and identity guidelines, such as the Health Insurance Portability and Accountability Act (HIPAA). Through the use of the centralized key management system, the present invention allows the entities to share their respective disparate personal data records (e.g., patient records) while complying with identity protection laws.

Specifically, each of the disparate entities is able to communicate with the centralized key management system to receive the information necessary to securely share personal data records with other entity's client computing devices. In particular, the personal data records are created and stored by the various entities and key information is stored and managed by the centralized key management system, such that centralized key management system does not maintain token data but only serves as a management hub for the use of keys to standardize tokens for the entities For example, a source client computing device may receive a distributed software engine including a hashing token, an encryption key for the source device, an encryption key for the destination device, and a processing template from the key management system. The processing template may be used to instruct the source client computing device how to transform the personal data records to a format used by the destination client computing device. The processing template may include instructions for combining raw personal data records with the hash token to create a personal identifier hash value (e.g., using a one way hashing function). Advantageously, the personal identifier hash value is created 'in process' and is subsequently encrypted using the source client computing device's encryption key. Once the encrypted personal identifier hash value is created, the processing template may instruct how the source client computing device can transform the encryption from the source device's encryption key format to that of a destination device's encryption key format. Accordingly, upon the transformation, the destination encrypted personal identifier hash value is delivered to the destination client computing device, such that the destination client computing device is able to access the underlying personal data record and personal information without requiring knowledge of the source client computing device's encryption scheme.

In accordance with aspects of the present invention, computing hardware devices are tied to the method steps, which include at least one transforming step. Specifically, the present invention involves multiple transformation steps necessarily tied to the computing hardware devices. Additionally, the transformation steps performed in the present invention are designed to provide an improvement necessitated by changes in technology (e.g., the creation of numerous disparate databases having their own systems for protecting privacy of data making sharing of data between the systems impractical) and that the present invention solves the problem created by these changes in technology (e.g., the need to be able to share and aggregate data from the disparate databases). Accordingly, the present invention is also an improvement to the technical area of database management and sharing the stored information on disparate databases (e.g., health care databases). Advantageously, the process of the present invention can further yield data that can be aggregated and analyzed for the purposes of valuable research, which conventional systems lack.

As would be appreciated by one skilled in the art, the present invention also dramatically increases the capabilities of entities to comply with federal and state privacy laws. In particular, the present invention allows for controlled sharing of disparate data by use of entity site level key management tied to business contracts. Accordingly, the process carried out in the present invention produces a consistent, repeatable and certifiably compliant method of protecting personal information, when sharing data, while still maintaining the rights of data sources to protect their data.

FIGS. 1 through 6, wherein like parts are designated by like reference numerals throughout, illustrate an example embodiment or embodiments of the centralized key management system for sharing personal data between the plurality of de-centralized entities, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, in a manner still in keeping with the spirit and scope of the present invention.

Figure 1:
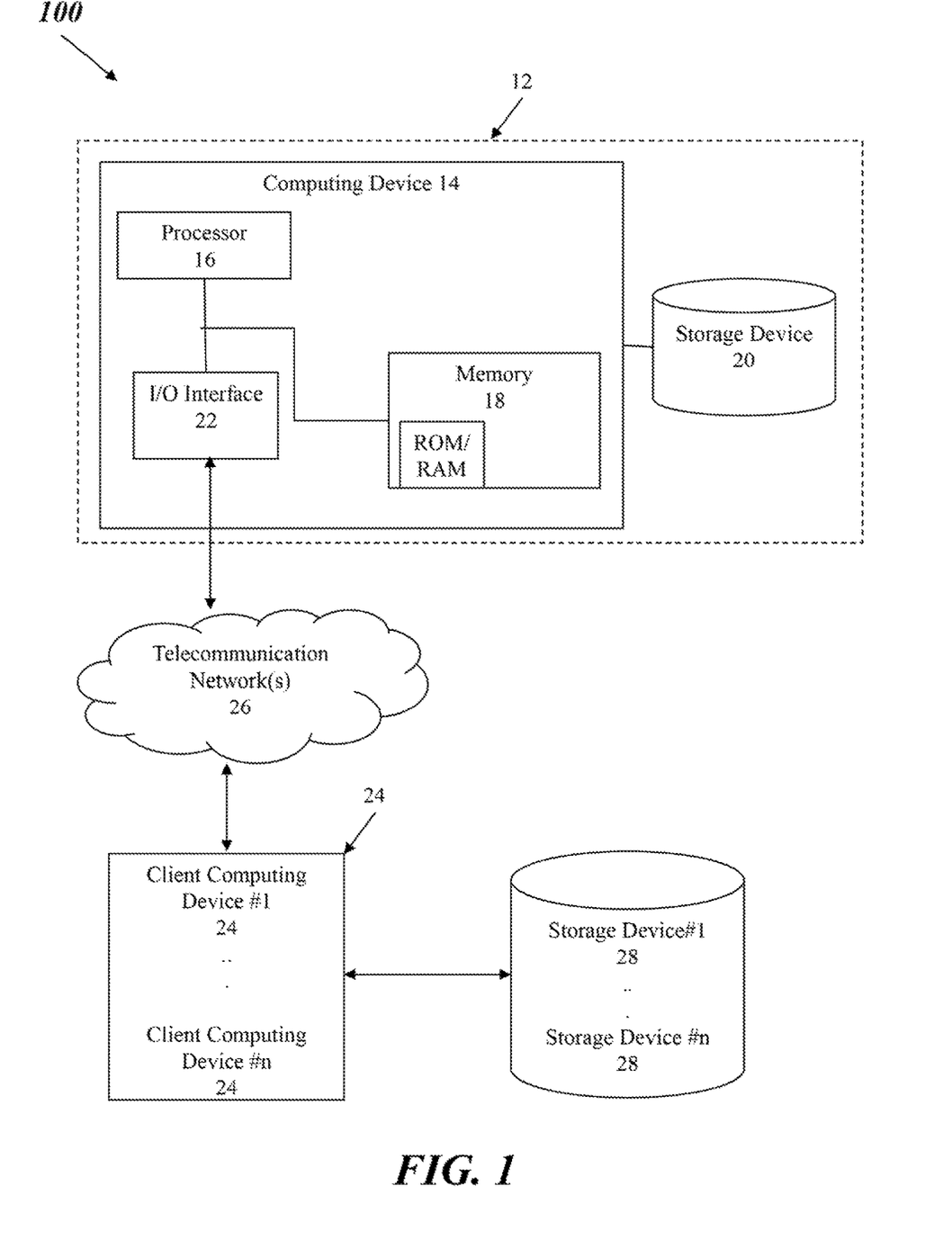
FIG. 1 is a diagrammatic illustration of a configuration for implementation of a key management system in accordance with the aspects of the invention.

FIG. 1 depicts a high level system architecture of implementing processes in accordance with aspects of the present invention. Specifically, FIG. 1 depicts a computing system 100 including a centralized key management system 12 including a computing device 14 having a processor 16, a memory 18, storage device 20, and an input/output interface 22. The centralized key management system 12, including the computing device 14, may be a general purpose computer or a specialized computer system. For example, the computing device 14 may include a single computing device, a collection of computing devices in a network computing system, a cloud computing infrastructure, or a combination thereof, as would be appreciated by those of skill in the art. In accordance with example embodiments, the computing device 14 may be a server system in communication with a database (e.g., storage device 20). Similarly, as would be appreciated by one of skill in the art, the storage device 20 may include any combination of computing devices configured to store and organize a collection of data. For example, the storage device 20 may be a local storage device on the computing device 14, a database storage component of the centralized key management system 12, a remote database facility, or a cloud computing storage environment. The storage device 20 may also include a database management system utilizing a given database model configured to interact with a user for analyzing the database data.

The computing system 100 of FIG. 1 may further include a plurality of client computing devices 24. Similar to the computing device 14, the client computing devices 24 may each include a single computing device, a collection of computing devices in a network computing system, a cloud computing infrastructure, or a combination thereof, as would be appreciated by those of skill in the art. Additionally, the client computing devices 24 may each include or otherwise be in communication with storage device(s) 28. As would be appreciated by one skilled in the art, the storage device(s) 28 may be similar to the storage device 20 in architecture and implementation. In accordance with example embodiments of the present invention, the plurality of client computing devices 24 may be de-centralized devices located remotely from the centralized key management system 12. For example, each of the plurality of client computing devices 24 may be independent institutions, organizations, and businesses, each collecting and storing a variety of personal data records.

Continuing with FIG. 1, the centralized key management system 12 may be configured to communicate and exchange data with the plurality of client computing devices 24. In accordance with an example embodiment of the present invention, the computing devices 12, 14, and 24 may be configured to establish a connection and communicate over telecommunication network(s) 24. For example, the centralized key management system 12 and the plurality of client computing device 24 may be configured to communicate over the telecommunication network(s) 26 using the input/output interface 22. As would be appreciated by one of skill in the art, the telecommunication network(s) 26 may include any combination of known networks. For example, the telecommunication network(s) 26 may be combination of a mobile network, WAN, LAN, or other type of network. The telecommunication network(s) 26 may be used to exchange data between the computing device 14 and the client computing devices 24, exchange data with the storage devices 20 and 28 (e.g., in a cloud environment), and/or to collect data from additional sources. For example, the client computing devices 24 may communicate with the key management system 12 to and exchange personal data records between multiple client computing devices 24 over the telecommunication network(s) 26.

In operation, the key management system 12 is responsible for managing encryption keys for the client computing devices 24 to facilitate securely sharing disparate personal data records stored by each of the client computing devices 24. In accordance with example embodiments of the present invention, the key management system 12 may be a trusted third party service provider responsible for managing encryption keys for the client computing devices 24. For example, the key management system 12 may manage encryption keys for two or more entities (e.g., at the entities; client computing devices 24) which have contracted to share their respective disparate personal data records (e.g., healthcare data records). Prior to exchanging personal data records between entities, each of the client computing devices 24 may register with the key management system 12. As would be appreciated by one skilled in the art, the registration process may include the creation of a new account for the registering party and a verification process to ensure that the registering party is a trusted entity. For example, each of the client computing devices 24 may provide the key management system 12 with credentials verifying that they are a legitimate entity. Additionally, in accordance with example embodiments of the present invention, the key management system 12 may require that each of the registering client computing devices 24 pay a subscription fee to use the services provided by the key management system 12. For example, as would be appreciated by one of ordinary skill in the art, the client computing devices 24 may be responsible for a monthly subscription fee to use the service.

Once registered, each of the client computing devices 24 are assigned a unique encryption key (or site level key) and a client computing device 24 identifier. Advantageously, the use of the encryption keys may be used by the key management system 12 to provide token management of the personal data records on each of the client computing devices 24. In accordance with example embodiments, the unique encryption keys may be created and assigned to each of the client computing devices 24 by the key management system 12. For example, at the time of registration, the key management system 12 will create a unique encryption key specific to the particular client computing device 24. The created unique encryption key may then be transmitted to the client computing device 24 to be associated with the unique encryption key within the key management system 12. Alternatively, in accordance with example embodiments, the client computing devices 24 may provide their own unique encryption key to be stored and implemented by the key management system 12. As would be appreciated by one of skill in the art, the key management system 12 may check the provided encryption key with existing encryption keys for previously registered client computing devices 24 to prevent duplicate keys. Accordingly, in the instance that the provided encryption key is not unique, the key management system 12 may request a new key or create a new unique encryption key for that particular client computing device 24.

In accordance with example embodiments of the present invention, the key management system 12 may further include business rules and legal and regulatory requirements. The business rules may be a set of rules for managing personal data records as implemented by the client computing devices 24 and may identify how the personal data records should be formatted for transmittal by that client computing device 24. Additionally, the business rules may control the use of segments of the data within the personal data records. For example, one data source may be restricted to identifying provider names, while other data sources may have geographic or sub-contractual restrictions. Similarly, the legal and regulatory requirements may be rules specific to the type of data being stored or exchanged by the client computing devices 24. For example, the key management system 12 may store rules implementing the HIPAA privacy regulations in the storage device 20, to be applied with respect to personal data records (e.g., patient health records) being exchanged between client computing devices 24. The key management system 12 may be configured to determine legal and regulatory requirements, by accessing the requirements in the storage device 20, associated with the business rules for the involved entities. In accordance with example embodiments of the present invention, the unique encryption keys may be created and/or deemed satisfactory based on the legal and regulatory requirements. Accordingly, the key management system 12 is responsible for hash token and encryption key management based on the business rules and legal and regulatory requirements of the client computing devices 24. For example, the key management system 12 ensures that the encryption keys to satisfy a certain level of encryption defined by the legal and regulatory requirements.

Continuing with FIG. 1, the key management system 12 may receive indication that two or more of the client computing devices 24 want to exchange personal data records. For example, the key management system 12 may receive an indication, in the form of a request, from a destination client computing device 24 to receive personal data records from a source client computing device 24. As would be appreciated by one skilled in the art, the request may be a request for a single personal data record (e.g., for a particular patient) or it may be a request for a batch of personal data records (e.g., all the records associated with a particular healthcare provider). Similarly, the request can include a request for all personal data records (for a particular patient) from a plurality of source client computing devices 24 and merge all of the received results for the particular personal data records. For example, one of the client computing devices 24 may issue a monthly batch request to one or more of the other client computing devices 24 for their respective personal data records.

In response to the indication of the request, the key management system 12 will compile a distributed software engine for the source client computing device(s) 24 (e.g., the source entities) supplying the requested personal data record(s). The distributed software engine may be used to facilitate a secure sharing of the personal health records between the source client device(s) 24 and the destination client computing device 24. In accordance with example embodiments of the present invention, the distributed software engine is created and/or compiled specifically for a particular transaction and for the specific client computing device(s) 24 involved in the transaction. For example, the distributed software engine is created to include the encryption keys associated with the participating client computing device(s) 24 (e.g., the source and destination client computing device(s) 24) and according to the business rule, regulations, and legal standards of the personal data records being exchanged by those client computing device(s) 24.

In accordance with example embodiments of the present invention, the distributed software engine may include an encryption token, a source client device encryption key unique to the source client device, a destination device encryption key unique to the destination device, and a processing template. Additionally, the distributed software engine may also include source libraries that are constructed according to the data stored by the key management system 12 (e.g., in a data vault). In accordance with example embodiments of the present invention, each code set for the distributed software engine is password protected, such that a password is required to initiate the execution of the processing template. According to one illustrative example embodiment, executing the processing template assists in the decryption of a master seed token and site specific encryption keys which are obfuscated in the actual code of the distributed software engine. Accordingly, upon execution, the encryption keys and master seed tokens are assembled using the password for decryption of the code. Those of skill in the art will appreciate there are other methods of processing that relying upon the teachings of the present description are considered to fall within the scope of the present invention. The encryption token may be combined with the requested personal data records by the source client computing device 24 to create a personal identifier hash value. For example, the processing template may instruct the client computing device(s) 24 to apply the encryption token using a particular one way hashing token. As would be appreciated by one skilled in the art, the encryption token may utilize a number of known encryption techniques. The source client computing device encryption key and the destination device encryption key are the unique encryption keys associated with the respective source and destination client computing devices 24, which are managed by the key management system 12. For example, the source client device encryption key and the destination device encryption key are the unique encryption key stored in the storage device 20 assigned and/or created during registration by the respective client computing devices 24.

In accordance with example embodiments of the present invention, the processing template provides instructions to the source client computing device 24 as to how to transform the personal data records in a format acceptable to and decipherable by the destination client computing device 24, as discussed in greater detail herein. For example, the processing template includes formatting rules for the personal data record(s) to be transmitted and transformed in compliance with the rules and regulations (e.g., HIPAA regulations). The processing template may be designed to validate the format of an input data source, define the data format scrubbing and modification rules for standardization and de-identification, define the hashing values/process to create a personal identifier hash value (e.g., hash token), and define a location of the personal identifier hash value in an output file. As would be appreciated by one skilled in the art, the processing template may also dictate the format of the output file. Additionally, the processing template may further be used in the transformation process to ensure that the data integrity of the personal data records remain intact. In accordance with example embodiments of the present invention, the processing template includes hardcoded instructions as to how to transform the personal data records. Advantageously, the hardcoded instructions enable a client computing device 24 to perform the transformation without to the knowing a destination client computing device's 24 unique encryption key. As would be appreciated by one skilled in the art, the key management system 12 may perform verification of each entity involved in the data transaction (e.g., the client computing devices 24) prior to providing the distributed software engine used for facilitating the data exchange.

In particular, the client computing devices 24 are operable to receive the distributed software engine from the key management system 12 and transform the personal data records using the processing template included therein. For example, a source client computing device 24 (e.g., the client device that receives the distributed software engine from the key management system 12) loads the encryption token, the unique source client device encryption key, the unique destination device encryption key, and the processing template into memory (e.g., memory 18). Once these core values are loaded, the processor (e.g., processor 16) loads the processing template as defined in the execution command of the distributed software engine. Upon execution, the processing template runs the commands necessary to transform the personal data records for securely sharing the personal data records with a disparate entity. For example, the source client computing device 24 may use the distributed software engine to share personal data records with another client computing device 24 (e.g., a destination client computing device 24) which utilizes a different encryption format. In accordance with example embodiments of the present invention, prior to execution, the process may employ a system check by processing a sanity test file, which is run each time the process is executed. A checksum value of the sanity test file results are compared to a base value to ensure the process, and the system that the process is run on, is operating correctly. For example, the sanity test file runs an example file and compares the resulting checksum value against a known value, if the checksum value is consistent with the known value, then the system is operating normally.

In accordance with example embodiments, the raw data for the personal data records may be standardized and de-identified by the client computing devices 24, in a consistent manner. Specifically, each person in the personal data records is de-identified by creating a standard token representing their identity and then encrypting it. The personal data (e.g., Last Name, First Initial, Date of Birth, Gender, etc.) is formatted and encrypted in a consistent manner. For example, the date format used throughout a person's personal healthcare data record is standardized in a MM/DD/YYYY format. Additionally, regulated private information (e.g., according to HIPAA guidelines) of the personal data records may be removed (e.g., de-identified). For example, a person's first and last name may be deleted from the personal data record being transmitted under the guidance of HIPAA. Subsequent to the standardization and de-identification, a hash token (e.g., a one way hashing process) is applied to the raw data of personal data record. As would be appreciated by one skilled in the art, the hash token may be the unique token provided by the key management system 12. In accordance with example embodiments of the present invention, the hash processing of the raw personal data record is performed entirely 'in process', such that the personal identifier hash value is not stored by the client computing device 24. For example, the personal identifier hash value is maintained in memory until the next processing step.

Once the raw personal data record has been hashed, the process advances to an encryption step. During the encryption step, the source client computing device encryption key (or site key) is applied to the personal identifier hash value to create an encrypted personal identifier hash value. In accordance with example embodiments of the present invention, the above processing steps may be performed to the personal data records associated with a request to share personal data records from another client computing device 24. As would be appreciated by one skilled in the art, the above processing steps may be performed to an entire collection of personal data records at any time after the registration with the key management system 12. For example, a source client computing device 24 may process each personal data record in an input file and generate an output row based on the processing template core values, such that an entire directory of source input files may be defined and the system will process all files outputting the result files to an output target directory. Additionally, the process may maintain a log to document any content issues with the input source data.

In accordance with example embodiments of the present invention, each of the client computing devices 24 may be configured to transform their secure and compliant personal data records to any other client computing device's 24 data sources format (e.g., encryption format). For example, a source client computing device 24 is configured to transform their respective personal data records into an encrypted format used by a destination client computing device 24. The source client computing device 24 may be configured to determine the encryption key (e.g., the unique destination device encryption key) associated with the at least one destination client computing device 24. As would be appreciated by one skilled in the art, the unique destination device encryption key may have previously been received by from the key management system 12. Once the destination encryption key has been identified, the source client computing device 24 may transform the encrypted personal identifier hash value from the source client encryption key format to the destination encryption key format associated with the destination client computing device 24. In accordance with example embodiments of the present invention, the transformation may be performed automatically using the distributed software engine, such that the source client computing device 24 does not have direct access to the destination encryption key. For example, the distributed software engine may be hardcoded with the instructions necessary to complete the transformation from the source format (e.g., the unique source encryption key) to the destination format (e.g., the unique source encryption key) without explicitly exposing the unique encryption key to the source client computing device 24.

Alternatively, in accordance with example embodiments of the present invention, the source client computing device 24 is given access to the destination encryption key, by the key management system 12, and handles the encryption itself. For example, the source client computing device 24 decrypts the personal identifier hash value using the source encryption key and then re-encrypts the personal identifier hash value using the destination encryption key. In accordance with example embodiments of the present invention, the process may be protected by an execution level password which is used to load the hash values and encryption keys to memory 18 during processing. For example, the source client computing devices 24 may not be able to access the encryption keys until the password has been verified by the key management system 12. Alternatively, in accordance with example embodiments of the present invention, the source client computing device 24 may initiate a call (e.g., an Application Program Interface call) to the key management system 12, requesting the encryption values from a secured password vault. For example, the source client computing device 24 may request the encryption keys from a centralized data vault. As would be appreciated by one skilled in the art, any of the core data supplied by the distributed software engine may be requested from the centralized data vault controlled by the key management system 12. After the transformation from the source encryption key to the destination encryption key is complete, the resulting destination encrypted personal identifier hash value may be transmitted to the destination client computing device 24. For example, the destination encrypted personal identifier hash value may be transmitted to a destination client computing device over the telecommunication network(s) 26 using a computing device identifier provided by the key management system 12.

Figure 2:
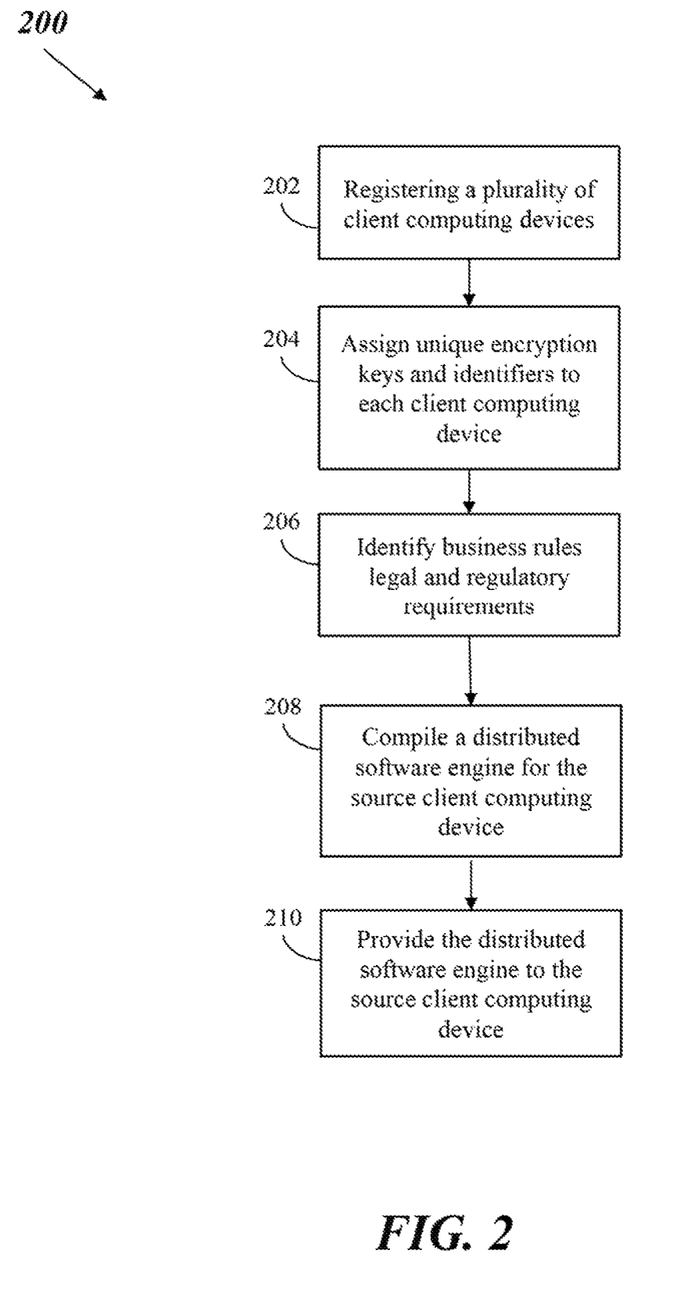
FIG. 2 is an illustrative flowchart depicting the operation of the key management system managing encryption keys for the plurality of client computing devices to facilitate a process of the secure sharing of disparate personal data records, in accordance with aspects of the invention.
Figure 3:
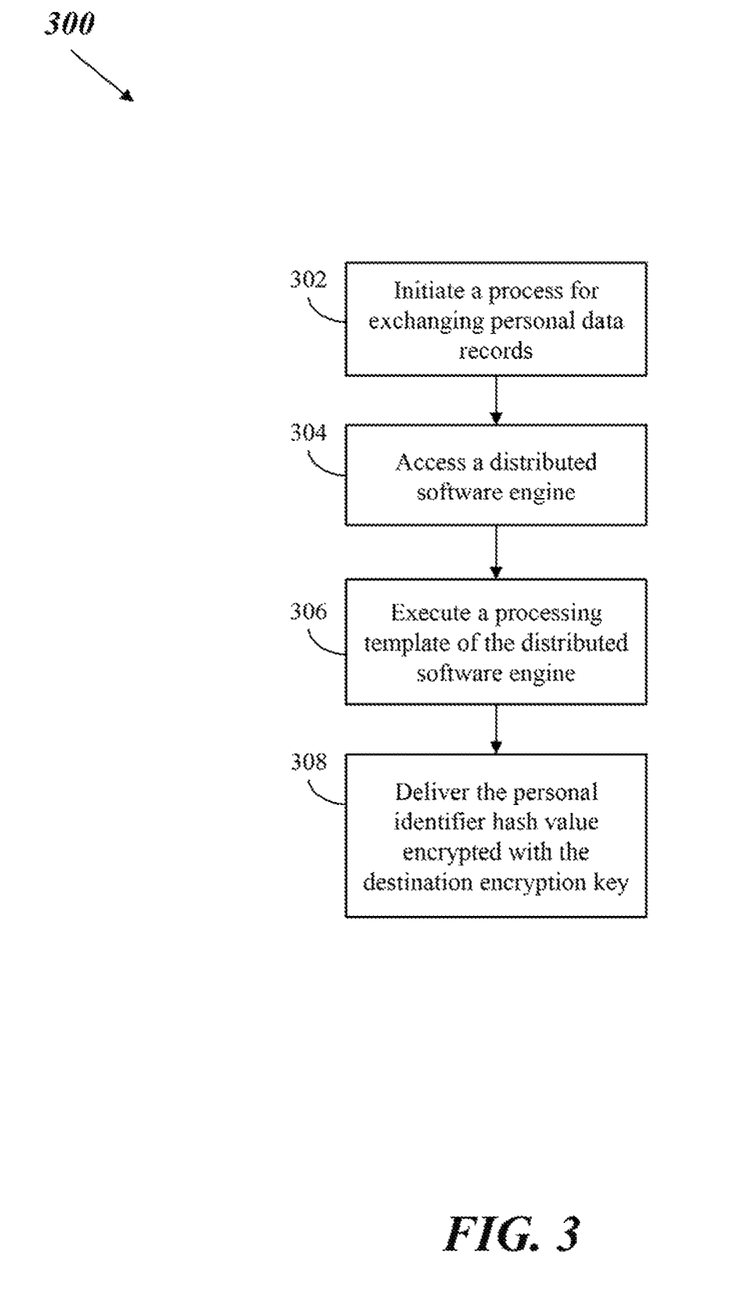
FIG. 3 is an illustrative flowchart depicting the operation process of the client computing devices when sharing personal data records, in accordance with aspects of the invention.
Figure 4:
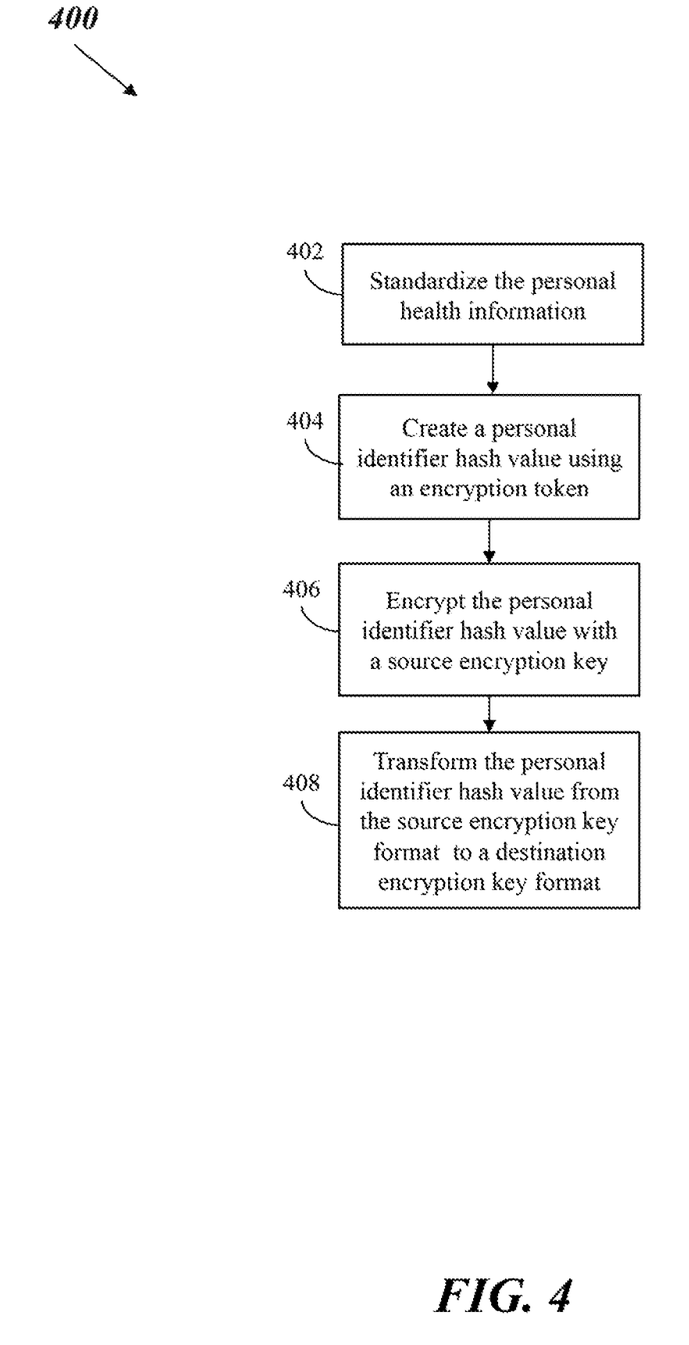
FIG. 4 is an illustrative flowchart depicting the operation process of the client computing devices when transforming the personal data records, in accordance with aspects of the invention.

FIGS. 2-4 show exemplary flow charts depicting implementation of the processes of the present invention. Specifically, FIG. 2 depicts an exemplary flow chart showing the operation of computing devices 12, 14, and 24. In particular, process 200 depicts the operation of the key management system 12 managing encryption keys for the plurality of client computing devices 24 to facilitate securely sharing of disparate personal data records stored by each of the plurality of client computing devices 12. At step 202, the key management system 12 registers a plurality of client computing devices 24, as discussed with respect to FIG. 1. At step 204, the key management system 12 assigns unique encryption keys and identifiers to each of the registered client computing devices 24, as discussed with respect to FIG. 1. As would be appreciated by one skilled in the art, the unique encryption keys and identifiers may be supplied by the client computing devices 24 and verified and stored by the key management system 12. At step 206, the key management system 12 identifies the business rules and legal and regulatory requirements associated with the registered client computing devices 24, as discussed with respect to FIG. 1. At step 208, in response to an indication that two or more client computing devices 24 request to share personal data records, the key management system 12 compiles a distributed software engine for each of the source client computing devices 24 (e.g., the client computing devices supplying the personal data records), as discussed with respect to FIG. 1. In accordance with example embodiments of the present invention, a distributed software engine may be compiled for each of the client computing devices 24 that have contracted to share personal data records with another client computing device 24. At step 210, the key management system 12 provides the distributed software engine to the appropriate source client computing devices 24, as discussed with respect to FIG. 1.

FIG. 3 depicts an exemplary flow chart showing the operation process of computing devices 12, 14, and 24. In particular, process 300 depicts the operation of the client computing devices 24 when sharing personal data records. At step 302, the client computing devices 24 initiate a process for exchanging personal data records between one or more other client computing devices 24, as discussed with respect to FIG. 1. As would be appreciated by one skilled in the art, the client computing devices 24 may initiate the exchange of personal data records by transmitting or receiving a request from another contracting client computing device 24. At step 304, the client computing devices 24 involved in the exchange may access a distributed software engine compiled by the key management system 12 for the particular client computing devices 24 involved in the transaction and the associated personal data records to be exchanged, as discussed with respect to FIG. 1. As would be appreciated by one skilled in the art, the distributed software engine may be received by the client computing devices 24 at the time of registration with the key management system 12 or may be received from the key management system 12 in response to initiating the personal data record exchange.

At step 306, the source client computing device(s) 24 execute the processing template included within the distributed software engine to create an encrypted personal identifier hash value, as discussed with respect to FIG. 1. In accordance with example embodiments of the present invention, prior to creating the encrypted personal identifier hash value, the processing template may request a login password to identify and to decrypt the hash seed tokens and encryption keys from the code included in the distributed software engine. For example, the hash seed tokens and encryption keys may be encrypted and obfuscated in the code and a password is required to decrypt and extract the hash seed tokens and encryption keys the code. During the execution of the distributed software engine the source client computing device(s) 24 modifies that raw personal data records being exchanged, such that the personal data records are securely standardized, de-identified, encrypted, and transformed into a personal identifier hash value encrypted in the format of the destination client computing device 24. As would be appreciated by one skilled in the art, portions of the distributed software engine may be performed prior to a request to exchange the personal data records. For example, all personal data records may be standardized, de-identified, and encrypted using the source client computing device's 24 unique encryption key prior to any initiation of an exchange of the personal data records. At step 308, the personal identifier hash value, encrypted using the destination client computing device's 24 encryption key, is delivered to the destination client computing device 24.

FIG. 4 depicts an exemplary flow chart showing the operation process of computing devices 12, 14, and 24. In particular, process 400 depicts the operation of the source client computing devices 24 standardizing and de-identifying raw personal data records, creating a hash token from the raw personal data records, encrypting the hash token, and transforming the encrypted hash token into a hash token encrypted in a destination client computing device's encryption format. At step 402, the source client computing device(s) 24 standardizes and de-identifies the raw personal data records, as discussed with respect to FIG. 1. At step 404, the source client computing device(s) 24 creates a personal identifier hash value using an encryption token. For example, the source client computing device(s) 24 combines the raw personal data record with the encryption token received from the key management system 12 using a one way hashing function. Advantageously, the hash token is created 'in process' only and is not stored by the source client computing device 24. At step 406, the source client computing device(s) 24 encrypts the personal identifier hash value using the encryption key for the source client computing device 24, as discussed with respect to FIG. 1. As would be appreciated by one skilled in the art, the personal identifier may be encrypted by using the unique encryption key assigned by the key management system 12 or by using its own unique encryption key. At step 408, the source client computing device(s) 24 transforms the personal identifier hash value from the source encryption key format to a destination encryption key format, as discussed with respect to FIG. 1.

Figure 5:
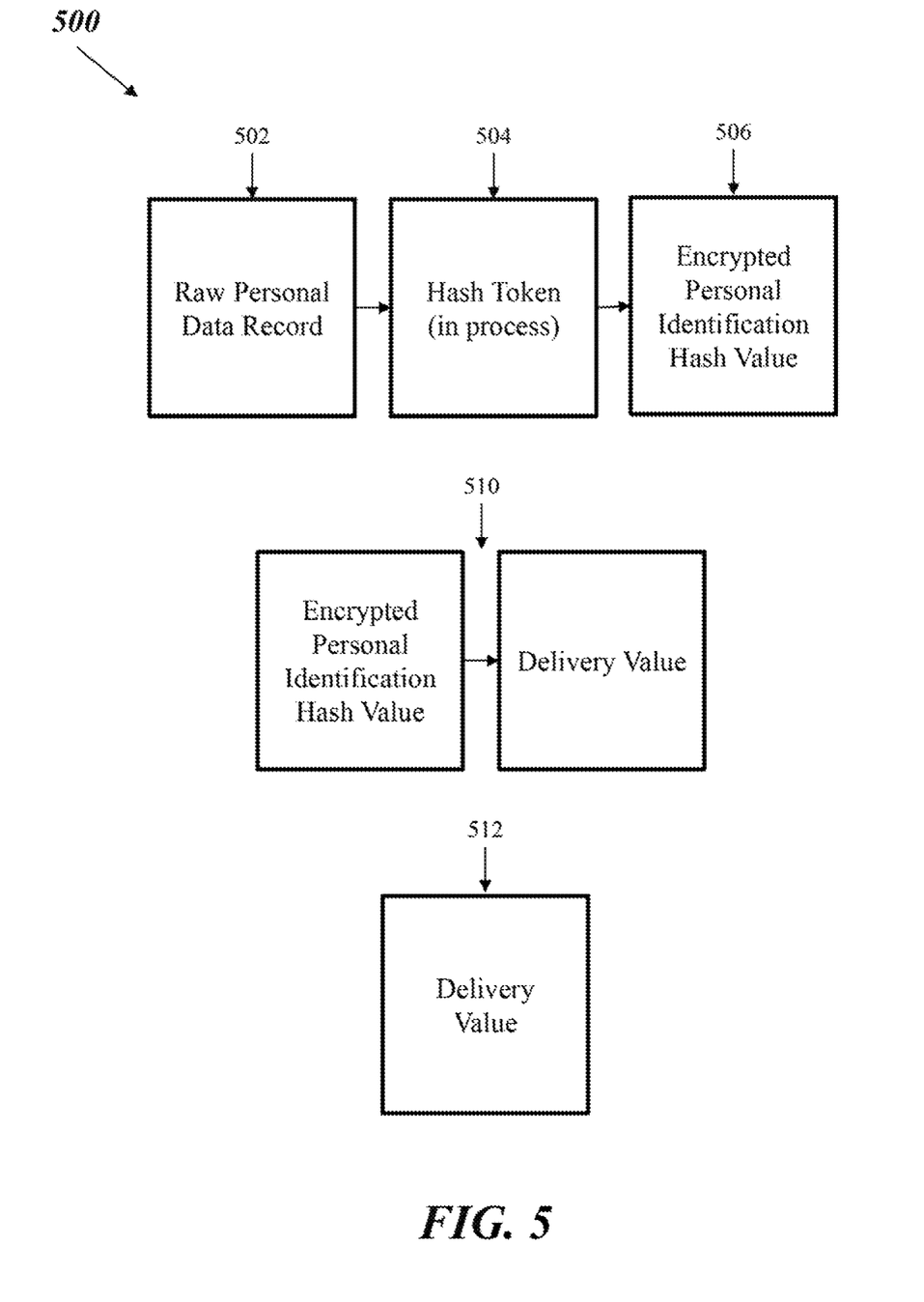
FIG. 5 is a diagrammatic illustration of a high level implementation of the transformation processes in accordance with aspects of the invention.

FIG. 5 shows a diagrammatic illustration of a high level implementation of the transformation processes in accordance with aspects of the invention. In particular, process 500 depicts the operation of the source client computing devices 24 as discussed with respect to FIG. 4. At step 502, the raw personal data record is standardized to form an initial input string, as discussed with respect to FIGS. 1 and 4. For example, data elements from the raw personal data record standardized and combined to form input string (e.g., last name, first name, date of birth, etc.). At step 504, the standardized personal data record is combined with a hash value to create a personal identifier hash value, as discussed with respect to FIGS. 1 and 4. For example, an in-process hash token is created when the raw personal data record is appended to a master seed value (hash value) and then processed using a one way hashing process. At step 506, the personal identifier hash value is encrypted using a source client computing device's 24 encryption key, as discussed with respect to FIGS. 1 and 4. For example, the personal identifier hash value represents an output value to the process when the source encryption key (or site key value) is applied to the in memory raw personal data record. At step 510, the encrypted personal identifier hash value, with the source client computing device's 24 encryption key, is transformed into a format encrypted with a destination client computing device's 24 encryption key, as discussed with respect to FIGS. 1 and 4. As would be appreciated by one skilled in the art, the transformation process may be performed by multiple sources and/or may be transformed for multiple destinations. For example, a source client computing device 24 may transform the encrypted personal identifier hash value to two different destination encryption formats for two different destination client computing devices 24. Step 512 represents the delivery value from the transformation process in which the encrypted personal identifier hash value has been converted to the representation of the encrypted personal identifier hash value for the destination client computing device 24. As would be appreciated by one skilled in the art, the destination client computing device 24 receives the encrypted personal identifier hash value and can decrypt it using its own encryption key.

Figure 6:
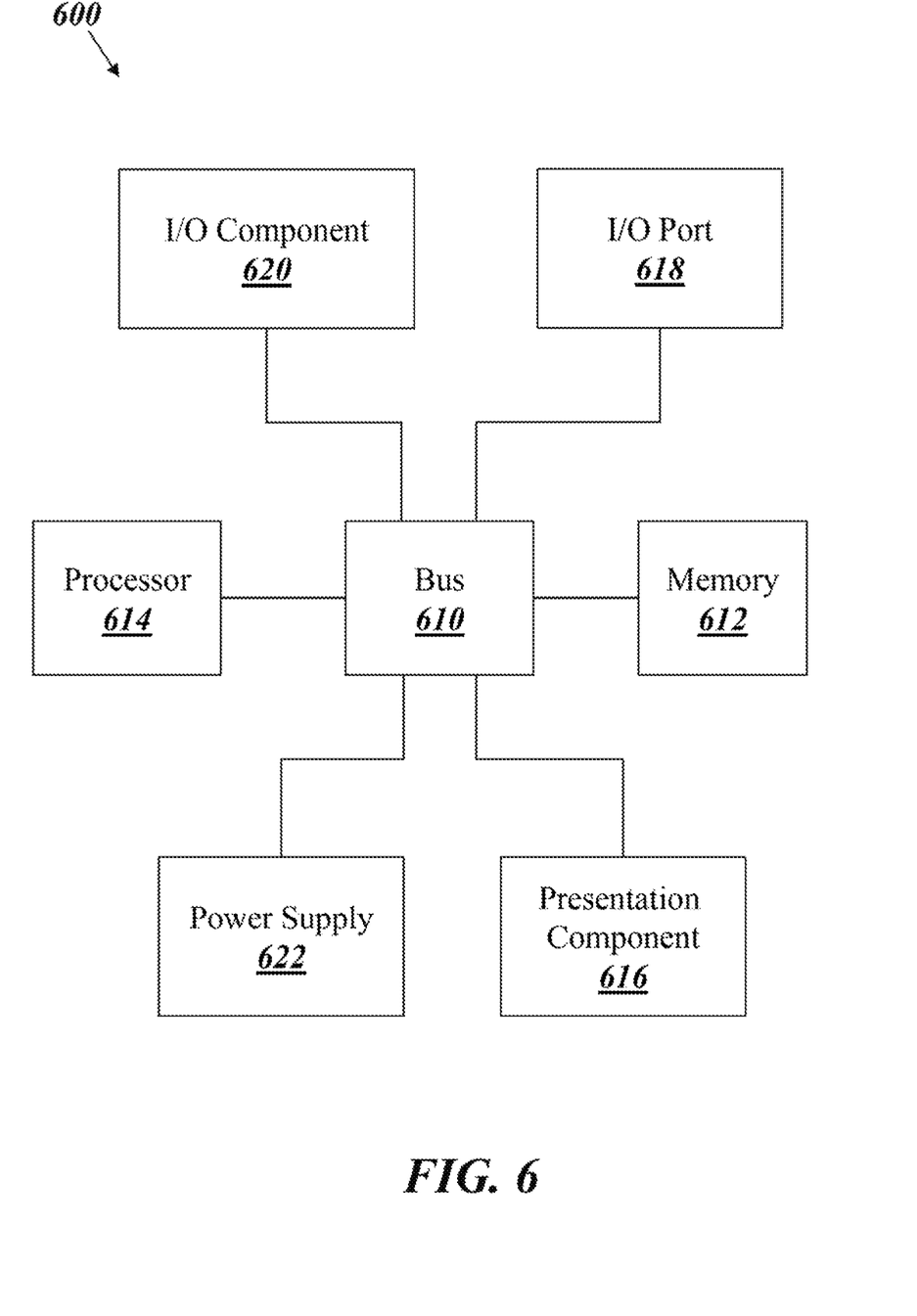
FIG. 6 is a diagrammatic illustration of a high level system architecture for devices implementing processes in accordance with aspects of the invention.

Any suitable computing device can be used to implement the computing devices 12, 14, 30 and methods/functionality described herein. One illustrative example of such a computing device 600 is depicted in FIG. 6. The computing device 600 is merely an illustrative example of a suitable computing environment and in no way limits the scope of the present invention. A "computing device," as represented by FIG. 6, can include a "workstation," a "server," a "laptop," a "desktop," a "hand-held device," a "mobile device," a "tablet computer," or other computing devices, as would be understood by those of skill in the art. Given that the computing device 600 is depicted for illustrative purposes, embodiments of the present invention may utilize any number of computing devices 600 in any number of different ways to implement a single embodiment of the present invention. Accordingly, embodiments of the present invention are not limited to a single computing device 600, as would be appreciated by one with skill in the art, nor are they limited to a single type of implementation or configuration of the example computing device 600.

The computing device 600 can include a bus 610 that can be coupled to one or more of the following illustrative components, directly or indirectly: a memory 612, one or more processors 614, one or more presentation components 616, input/output ports 618, input/output components 620, and a power supply 624. One of skill in the art will appreciate that the bus 610 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 6 is merely illustrative of an exemplary computing device that can be used to implement one or more embodiments of the present invention, and in no way limits the invention.

The computing device 600 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 600.

The memory 612 can include computer-storage media in the form of volatile and/or nonvolatile memory. The memory 612 may be removable, non-removable, or any combination thereof. Exemplary hardware devices are devices such as hard drives, solid-state memory, optical-disc drives, and the like. The computing device 600 can include one or more processors that read data from components such as the memory 612, the various I/O components 616, etc. Presentation component(s) 616 present data indications to a user or other device. Exemplary presentation components include a display device, speaker, printing component, vibrating component, etc.

The I/O ports 618 can enable the computing device 600 to be logically coupled to other devices, such as I/O components 620. Some of the I/O components 620 can be built into the computing device 600. Examples of such I/O components 620 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for distributing universally shareable personal health data in compliance with legal and regulatory requirements, the method comprising:
   storing, by a source client device, personal health data;
   creating, by a key management system, a distributed software engine, wherein the distributed software engine comprises:
      an encryption token;
      a source client device encryption key unique to the source client device;
      a destination client device encryption key unique to the destination client device; and
      a processing template;
   receiving from the key management system, by the source client device, the distributed software engine over a telecommunication network;
   de-identifying, by the source client device, the personal health data, using the received distributed software engine, wherein the de-identifying the personal health data comprises:
      executing the processing template, wherein the executing the processing template comprises:
         formatting the personal health data;
         creating a personal identifier hash value by combining the formatted personal health data with the encryption token; and
         encrypting the personal identifier hash value with the source client device encryption key unique to the source client device;
      decrypting the encrypted personal identifier hash value and re-encrypting the decrypted personal identifier hash value using the destination client device encryption key unique to the destination client device; and
   transmitting, by the source client device, the re-encrypted personal identifier hash value to the destination client device.

2. The method of claim 1, further comprising:
   creating, by the key management system, one or more distributed software engines for one or more source client devices or destination client devices.

3. The method of claim 1, wherein creating the distributed software engine comprises creating each distributed software engine by a trusted third party server of the key management system.

4. The method of claim 1, further comprising:
   requesting, by the distributed software engine, a password to access at least one of the encryption token, the source client device encryption key, the destination client device encryption key, and the processing template of the distributed software engine.

5. The method of claim 1, further comprising:
   registering and verifying, by the key management system, two or more entities; and,
   requesting, by the distributed software engine, the encryption token, the source client device encryption key, the destination client device encryption key, and the processing template from a data vault of the key management system.

6. The method of claim 5, further comprising:
   registering, by the key management system, a source client device or at least one client destination device; and
   wherein the method further comprises one of:
      providing, by the key management system, a unique encryption key, or
      creating, by the key management system, a client device encryption key and a client device identifier.

7. The method of claim 1, further comprising:
   receiving, by the distributed software engine at the source client device, a request from the destination client device to share the personal health data.

* * * * *

UNITED STATES PATENT AND TRADEMARK OFFICE
CERTIFICATE OF CORRECTION

Page 1 of 1

PATENT NO. : 10,910,089 B2
APPLICATION NO. : 15/045605
DATED : February 2, 2021
INVENTOR(S) : Joseph R. Austin and Shahir Kassam-Adams It is certified that error appears in the above-identified patent and that said Letters Patent is hereby corrected as shown below:

On the Title Page

In the Applicant (71) section delete, "Universal Patient Key, Inc., Sterling, MA (US)" and insert, --Datavant, Inc., San Francisco, CA (US)--.

In the Assignee (73) section delete, "UNIVERSAL PATIENT KEY, INC., Sterling, MA (US)" and insert, --DATAVANT, INC., San Francisco, CA (US)--.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*